US012781172B2

(12) United States Patent
Pizzi et al.

(10) Patent No.: US 12,781,172 B2
(45) **Date of Patent: *Nov. 3, 2026**

(54) STERILE SENSOR INSERTION

(71) Applicant: Global Life Sciences Solutions USA LLC, Marlborough, MA (US)

(72) Inventors: Vincent Francis Pizzi, Westborough, MA (US); Jeffrey Carter, Westborough, MA (US); Ralph Stankowski, Westborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 1029 days.

This patent is subject to a terminal disclaimer.

(21) Appl. No.: 18/045,789

(22) Filed: Oct. 11, 2022

(65) Prior Publication Data

US 2024/0117289 A1 Apr. 11, 2024

(51) Int. Cl.
*C12M 1/04* (2006.01)
*C12M 1/00* (2006.01)

(52) U.S. Cl.
CPC ............ *C12M 27/04* (2013.01); *C12M 23/14* (2013.01); *C12M 23/28* (2013.01)

(58) Field of Classification Search
CPC ...... C12M 27/04; C12M 23/14; C12M 23/28; C12M 41/00; C12M 37/04
See application file for complete search history.

(56) References Cited

U.S. PATENT DOCUMENTS 5,939,610 A 8/1999 Iwamoto et al.
7,901,934 B2 3/2011 Kunas et al.
7,927,316 B2 4/2011 Proulx et al.
8,607,432 B2 12/2013 Matkovich et al.
8,631,716 B2 1/2014 Bernard et al.
(Continued)

FOREIGN PATENT DOCUMENTS

DE 3834240 A1 4/1990
DE 102004015703 A1 11/2005
(Continued)

OTHER PUBLICATIONS

International Search Report and Written Opinion regarding International Application No. PCT/EP2015/067589, mail date Dec. 16, 2015, 8 pages.
(Continued)

*Primary Examiner* — William H. Beisner
*Assistant Examiner* — Danielle B Henkel
(74) *Attorney, Agent, or Firm* — Eversheds-Sutherland (US) LLP

(57) ABSTRACT

The present invention provides a system for the insertion of a pre-sterilized sensor probe into a sterile vessel. The system of the invention provides a reliable and straightforward way to insert one or more sterile probes into a sterile vessel. The present invention also provides a sterile vessel that includes one or more of the systems of the invention. The sterile vessel can be a flexible or semi-rigid bag or tubing of the type typically used for carrying out biochemical and/or biological processes and/or manipulating liquids and other products of such processes. Furthermore, the present invention provides a method for aseptically inserting a probe into a sterile vessel where the method makes use of the system of the invention.

19 Claims, 8 Drawing Sheets

(56) References Cited

U.S. PATENT DOCUMENTS

| | | | |
|---|---|---|---|
| 9,046,501 B2 | 6/2015 | Loebbert et al. | |
| 9,056,695 B2 | 6/2015 | Bernard et al. | |
| 9,103,703 B2 * | 8/2015 | Baumfalk | C21C 5/527 |
| 2001/0028865 A1 | 10/2001 | Cummings et al. | |
| 2005/0229727 A1 | 10/2005 | Caderas | |
| 2007/0185472 A1 | 8/2007 | Baumfalk et al. | |
| 2008/0048436 A1 | 2/2008 | Matkovich et al. | |
| 2010/0255526 A1 * | 10/2010 | Braet | B01F 31/42<br>435/29 |
| 2011/0201100 A1 | 8/2011 | Proulx et al. | |
| 2011/0236962 A1 | 9/2011 | Loebbert et al. | |
| 2013/0063843 A1 | 3/2013 | Chen et al. | |

FOREIGN PATENT DOCUMENTS

| | | | |
|---|---|---|---|
| EP | 1855088 | A2 | 11/2007 |
| WO | 92/01218 | A1 | 1/1992 |
| WO | 2004/023127 | A1 | 3/2004 |
| WO | 2010017519 | A1 | 2/2010 |
| WO | 2010145747 | A1 | 12/2010 |
| WO | 2012/082974 | A1 | 6/2012 |
| WO | 2013063550 | A1 | 5/2013 |

OTHER PUBLICATIONS

GB Search Report regarding GB Application No. 1415636.8, dated May 27, 2015, 4 pages.

Chinese Office Action for CN Application No. 201580042572.9, mailed Sep. 5, 2019 (15 pages with English Translation).

Summons to Attend Oral Proceedings of Oct. 11, 2021, mailed Nov. 10, 2021.

* cited by examiner

STERILE SENSOR INSERTION

CROSS REFERENCE TO RELATED APPLICATIONS

This application is a continuation of U.S. patent application Ser. No. 15/500,623, filed Jan. 31, 2017, issued as U.S. Pat. No. 11,499,126 on Nov. 15, 2022, which claims the priority benefit of PCT/EP2015/067589 filed on Jul. 30, 2015, which claims priority to U.S. Provisional Application No. 62/034,819 filed on Aug. 8, 2014 and GB Application No. 1415636.8 filed Sep. 4, 2014, the entire contents of which are hereby incorporated by reference herein.

TECHNICAL FIELD OF THE INVENTION

The present invention relates generally to bioprocessing systems and methods. Specifically, the invention relates to systems and methods for inserting sensors into bioreactor vessels and tubing, including flexible or semi-rigid bags or tubing.

DESCRIPTION OF RELATED ART

A variety of vessels, devices, components and unit operations are known for carrying out biochemical and/or biological processes and/or manipulating liquids and other products of such processes. Increasingly, in order to avoid the time, expense, and difficulties associated with sterilizing the vessels used in biopharmaceutical manufacturing processes, single-use or disposable bioreactor bags and single-use mixer bags are used as such vessels. For instance, biological materials (e.g., animal and plant cells) including, for example, mammalian, plant or insect cells and microbial cultures can be processed using disposable or single-use mixers and bioreactors.

The manufacturing of complex biological products such as proteins (e.g., monoclonal antibodies, peptides, hormones, and vaccine immunogens) requires, in many instances, multiple processing steps ranging from cell culture (bacteria, yeast, insect, fungi, etc.) and/or fermentation, to primary recovery, purification, and others. Conventional bioreactor-based manufacturing of biological products generally utilizes batch, or fed-batch processing through a series of unit operations with subsequent off-line laboratory analysis conducted on representative samples collected from various points of the process to ensure quality.

In order to obtain timely information regarding changing conditions within a bioreactor vessel during its operation, the use of sensor technology has been employed. With regard to use of disposable bioreactors, there are recognized difficulties in sterilely inserting a sensor into a flexible-walled bioreactor or flexible tubing that feeds or drains such vessels. Further, optical, electrical, and pH sensors, for example, cannot undergo sterilization via Gamma irradiation or be positioned inside a flexible bag or tubing and require an attachment means that allows for a clear signal to be communicated to or from external analytical instrumentation.

An example of aseptic insertion of a probe at the point of use is described in U.S. Pat. No. 7,901,934 (Hyclone, Kunas et al). This patent describes a probe assembly that includes a flexible sleeve having a sterile interior within which the sterilized probe is positioned. The sleeve includes one side of a sterile connector, the other side of which is present on a stirred-tank bioreactor system. The probe is attached by mating both sides of the sterile connector and then the prove sensor tip is pushed into the bioreactor as the flexible sleeve compresses.

WO2010145747A1 (Sartorious, Baumfalk et al) describes a sensor device comprising an optical sensor, a container and a compartmentalization means, which permits the sensor to remain in a sterile calibration position prior to insertion.

US20110201100A1 (Millipore, Proulx et al) describes the Millipore SensorReady™ system for aseptic insertion of sensors into an external manifold aligned in a flowpath instead of a bag. This provides some flexibility in configuration with standard bag but the sensors are not directly in contact with the bulk contents of the bioreactor.

A sensor that is moved through sterile calibration chambers prior to insertion into a bioreactor is described in US20110236962A1 (Hamilton, Loebbert and Schoenfuss).

WO2013063550 (Xcellerex, Damren et al) describes a probe assembly where the sterile probe is held within the sterile interior of a sheath that is at least partly rigid. The sheath connects to a bioreactor using sterile face connectors and the probe is pushed into the bioreactor by means of an actuator.

There is an ongoing need for an improved sensor connector and a method for inserting a sensor into flexible disposable bioreactor bags or fluid circulating tubing. An improved device and method for sterilely inserting a non-disposable sensor or a disposable sensor into a flexible bioreactor bag or tubing would also be beneficial for use in bioreactor-based manufacturing systems that include in-line sensing in order to provide real-time data.

Because the sensor itself can be expensive, there is also an ongoing need for an improved device and method for sterilely inserting a sensor into a flexible bag or tubing, a device and method that facilitate the removal of the sensor from the disposable bag or tubing without damaging the sensor. With such an improved device and method, the bag or tubing can be discarded along with the sensor, or alternatively the sensor can be removed, re-sterilized, and re-used.

SUMMARY OF THE INVENTION

In accordance with the present invention there is provided a system for the insertion of a pre-sterilized sensor probe into a sterile vessel. The system of the invention includes a body with a plunger positioned therein with the pre-sterilized sensor probe positioned within the plunger. The system includes liquid-tight seals to maintain sterility of the probe during use. Suitable seals include configurations well-known the skilled person, including but not limited to o-rings, overmoulded seals, etc. Once the system of the invention has been connected to the vessel using a sterile connection system, a handle of the system that cooperates with the plunger directs movement of the probe into the sterile vessel.

In one embodiment the handle is rotated around the longitudinal axis of said system to direct movement of the plunger into the sterile vessel. In one embodiment the movement of the plunger is linear.

The system of the invention provides a reliable and straightforward way to insert one or more sterile probes into a sterile vessel.

The present invention also provides a sterile vessel that includes one or more of the systems of the invention. The sterile vessel can be a flexible or semi-rigid bag or tubing of the type typically used for carrying out biochemical and/or biological processes and/or manipulating liquids and other products of such processes. Commonly, single-use or disposable bioreactor bags and single-use mixer bags are used as such vessels.

The present invention also provides a method for aseptically inserting a sterile probe into a sterile vessel where the method makes use of the system of the invention.

The insertion of a reusable probe into a sterile vessel at point of use is known in the art as previously described herein. The current invention in contrast provides means enabling the insertion of a single-use probe where the probe requires a means of sterilization other than ionizing gamma radiation or heat. The invention makes use of a septum port and a modified aseptic connection, commercially-available examples of which include Kleenpak™ from Pall, ReadyMate™ from GE Healthcare and AseptiQuik™ from Colder. This provides a sterile barrier between the seal and the contents of the sterile vessel. The advancement of a probe through the mating connector septum port into the sterile vessel is actuated through a rotation of either a barrel (for example in FIG. 7) or a rotating bezel engaging a threaded barrel (for example in FIG. 1). In certain embodiments once the probe is fully inserted a locking tab prevents the intentional or accidental reversing the sensor probe engagement from the septum port.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being placed upon illustrating the principles of the invention. Those skilled in the art will understand that the devices and methods specifically described herein and illustrated in the accompanying drawings are non-limiting exemplary embodiments. The features illustrated or described in connection with one exemplary embodiment can be combined with the features of other embodiments. Such modifications and variations are intended to be included within the scope of the present invention.

DETAILED DESCRIPTION OF THE PREFERRED EMBODIMENTS

Figure 1:
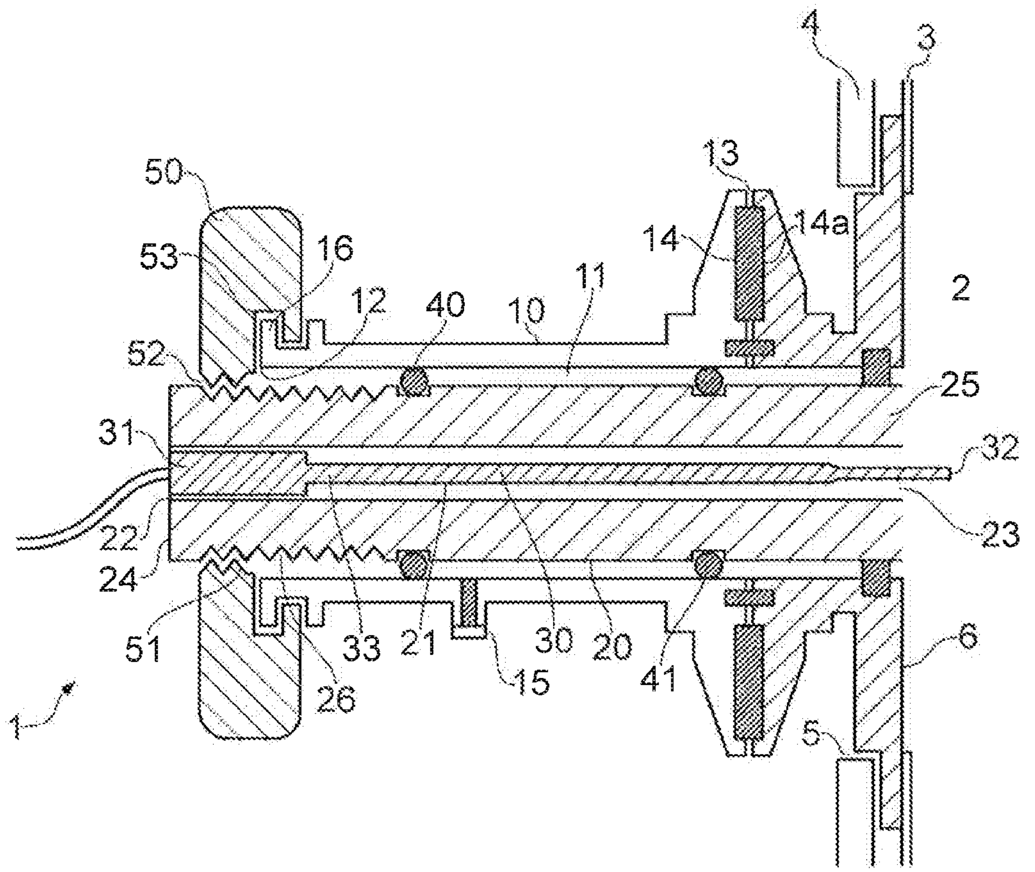
FIG. 1 is a cross-sectional view of an exemplary system of the present invention connected to a bioreactor and with the probe inserted.

To more clearly and concisely describe and point out the subject matter of the claimed invention, the following definitions are provided for specific terms used throughout the present specification and claims. Any exemplification of specific terms herein should be considered as non-limiting examples.

The term "sterile probe" refers to a device useful in the measurement of one or more physical, chemical or biological properties of a substance, in particular where that substance is a solution, where the device has been sterilized. The term "probe" may be used interchangeably with the word "sensor". The present invention is suitable for insertion of any sterile probe into a sterile vessel, but is particularly suitable for the insertion of a pre-sterilized probe, i.e. one that requires a means of sterilization other than ionizing gamma radiation or heat, e.g. sterilization using ethylene oxide.

A "sterile vessel" can be any vessel having a sterile interior. More particularly the term sterile vessel is intended to cover any vessel used to contain a particular biological material without being contaminated by any other biological material. Such a vessel may also be known as a "biocontainer" and non-limiting examples include bioreactors, intermediate reactor vessels and bioprocessing devices. In a particular example, a sterile vessel can be a flexible bag contained within a rigid holder (e.g. made from stainless steel)

The "body" of the system of the invention is a substantially rigid and cylindrical component.

The term "substantially" as used herein encompassing the pure definition of the term with which it is used as well as embodiments that can for the most part be defined as that particular term.

The term "sterile face connection" as used herein refers to any means permitting the sterile connection, or "mating" of two opposing planar surfaces. Commonly-used sterile face connections are single-use aseptic connections, a non-limiting example of which is the Readymate™ connector.

The term "plunger" as used herein is taken to mean a component, substantially rigid and cylindrical like the above-described body, but configured to moveably fit within said body. The term "moveably" is intended to refer generally to the property of being able to be moved by hand with relative ease, applying a routine level of effort to permit movement of the plunger in a direction along the central axis of the body. The term "diameter less than" in this context can be understood more specifically to mean of a diameter only slightly less than, e.g. such that when seals are fitted to the outer surface of the plunger a liquid-tight seal is formed.

The term "channel" as used herein is taken to mean a substantially tubular passage within which a component or a substance can be contained.

The term "secured within" used herein to describe the relationship of the sterile probe with the inner channel of the plunger is intended to mean secured to the extent that with any routine movement of the plunger, the sterile probe is also moved. Means for securing the sterile probe within the plunger might include use of adhesive or connectors applied between the sterile probe and the inner surface of the plunger, or by using a variety of other securing means well-known to the skilled person, as long as said means does not interfere with the normal operation of the probe.

The term "electrical connection" refers to any well-known means connecting the sterile probe to a supply of electricity suitable to permit functioning of the probe.

The term "handle" refers to an attachment that allows movement to be applied by hand. While a variety of configurations are possible, the handle should be strong enough to transmit the force required to move the plunger within the body, long enough so that a hand can grip it reliably to exert that force, and sufficiently small so that a hand can surround it enough to grip it as solidly as required to exert that force.

The term "sterilization port" refers to an opening in said body that allows the penetration of sterilizing gas, e.g. ethylene oxide or peroxide, into the sterile bore (11). This is facilitated through a sterile porous barrier, a non-limiting example of which is Tyvek™.

The term "thread" as used in connection with the plunger and the handle in certain embodiments refers to co-operating screw threads, one on certain parts of the outer surface of the plunger and one on the internal surface of the handle. Such threads are well-known in the mechanical arts to convert rotational force into linear movement, as applied in certain embodiments of the present invention.

The term "notch" means an indentation or incision on an edge or surface. Specifically in the context of the present invention a notch is configured to be received into a recess, for example to permit two elements to be associated with or to co-operate with each other.

The term "cam" as used herein refers to a rotating piece used to transform rotary motion into linear motion.

The term "locked" as used herein refers to being rigidly fixed or immovable. Specifically the term is used to refer to wherein the plunger is locked into the second position, wherein the probe is positioned within the sterile vessel. Examples of locking mechanisms suitable for application to the present invention are described in U.S. Pat. No. 7,927,316.

The term "sheath" refers to a close-fitting protective cover for the sensor end of the probe that at the same time as protecting the sensor allows liquid to flow and contact the sensor allowing it to function. Non-limiting examples of sheaths suitable for use with the present invention are illustrated in FIGS. 3D and 3E.

In a first aspect the present invention provides a system (1) for insertion of a sterile probe (30) into a sterile vessel (2) wherein said system comprises:

(i) a body (10) formed of plastic and having a sterile bore (11) formed through at least a portion of its interior, the body (10) having a first (12) and second (13) end, the second end (13) comprising a body sterile face connection (14);

(ii) a plunger (20) formed of plastic and contained within the sterile bore (11) of the body (10), the plunger (20) having a shape substantially corresponding to that of said sterile bore (11) and being of a diameter less than said sterile bore (11), the plunger (20) also having an inner channel (21) opening onto a first aperture (22) on a first end (24) of said plunger (20) and a second aperture (23) on a second end (25) of said plunger (20), wherein said first (24) and second (25) ends of said plunger (20) correspond respectively to said first (12) and second (13) ends of said body (10), and wherein said plunger (20) is moveable between a first position and a second position;

(iii) a sterile probe (30) secured within the inner channel (21) of said plunger (20) wherein said sterile probe (30) comprises an electrical connection end (31) substantially aligned with said first end (24) of said plunger (20), a sensor end (32) substantially aligned with said second end (25) of said plunger (20), and a sensor body (33) therebetween;

(iv) one or more seals (40, 41, 42) between the plunger (20) and the sterile bore (11) to form a liquid-tight seal between various portions of the plunger (20) and the sterile bore (11); and, (v) a handle (50) cooperating with said plunger (20) to direct movement of said plunger (20) within the sterile bore (11) between said first position and said second position.

In one embodiment of the system (1) of the invention the sterile probe (30) is selected from the group comprising metabolic, biologic, and physical sensors. In another more particular embodiment, said sterile probe is a glucose sensor, a lactate sensor, a pH sensor, a temperature sensor, a conductivity sensor or a cell mass and cell viability sensor.

In one embodiment of the system (1) of the present invention, each of said body (10) and said plunger (20) is independently formed of a plastic selected from the group consisting of polyetherimides (PEI), polyetheretherketone (PEEK), polyetherketone (PEK), polysulphones, polyarylsulphones, polyalkoxysulphones, polyethersulphones, polyphenyleneoxide, polyphenylenesulphide, polycarbonate, and blends thereof.

In one embodiment of the system (1) of the present invention illustrated in FIG. 1, said body (10) further comprises a sterilization port (15).

In one embodiment, the system (1) of the present invention further comprises one or more seals (70, 71) between the sterile probe (30) and the inner channel (21) of said plunger (20).

In one embodiment of the system (1) of the present invention said handle (50) is rotated around the longitudinal axis of said system (1) to direct movement of said plunger (20) within the sterile bore (11) between said first position and said second position. In a particular embodiment the movement of the plunger is linear.

In one embodiment of the system (1) of the present invention, between said first end (24) and said one or more seals (40, 41, 42), said plunger (20) comprises a plunger thread (26) on its outer surface, said handle (50) comprises a central opening (52) of dimensions suitable to accommodate the width of said plunger (20) and wherein said central opening (52) comprises a handle thread (51) that cooperates with said plunger thread (26) such that rotational movement of said handle (50) directs the movement of said plunger (20) within the sterile bore (11) between said first position and said second position. An example of this embodiment is illustrated in FIG. 1.

In one embodiment of the system (1) of the present invention said central opening (52) further comprises a recess (53) and said body (10) comprises a first notch (16) protruding outwardly from its surface and located substantially at its first end (12), wherein said first notch (16) is received in said recess (53).

In one embodiment of the system (1) of the present invention said body (10) further comprises a second notch (16*a*) protruding outwardly from the surface of said body (10) wherein said second notch (16*a*) provides mechanical support to the interaction of said first notch (16) and said recess (53).

Figure 7:
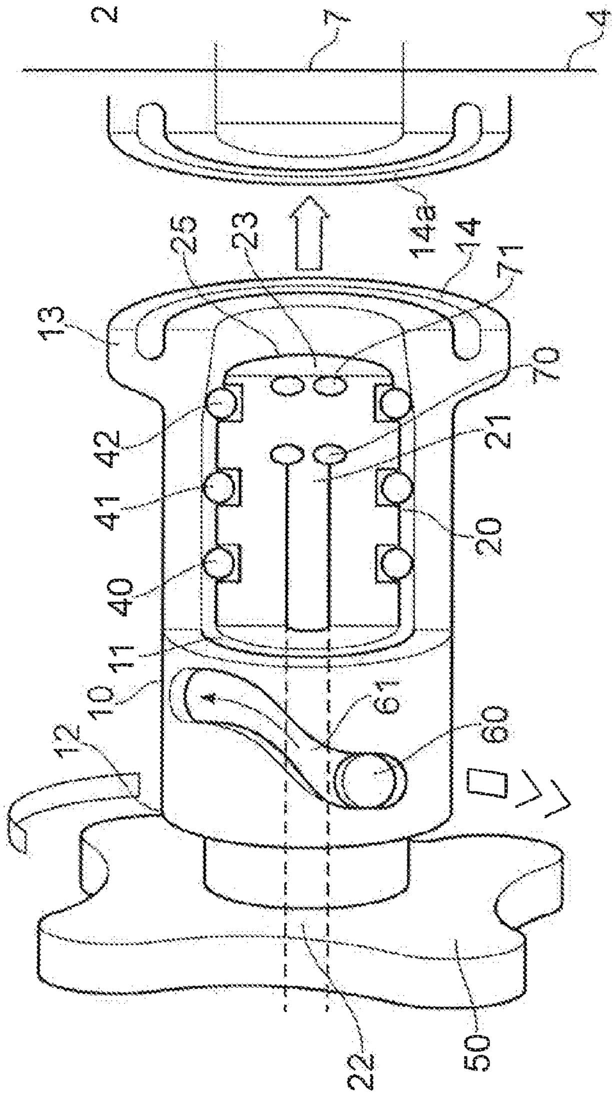
FIG. 7 shows a sensor probe and a modified ReadyMate™ connection system that can be used as exemplary body and plunger parts of the invention. A bioreactor with a sterile face connector is also shown, including a septum into which the probe can be inserted.
Figure 8:
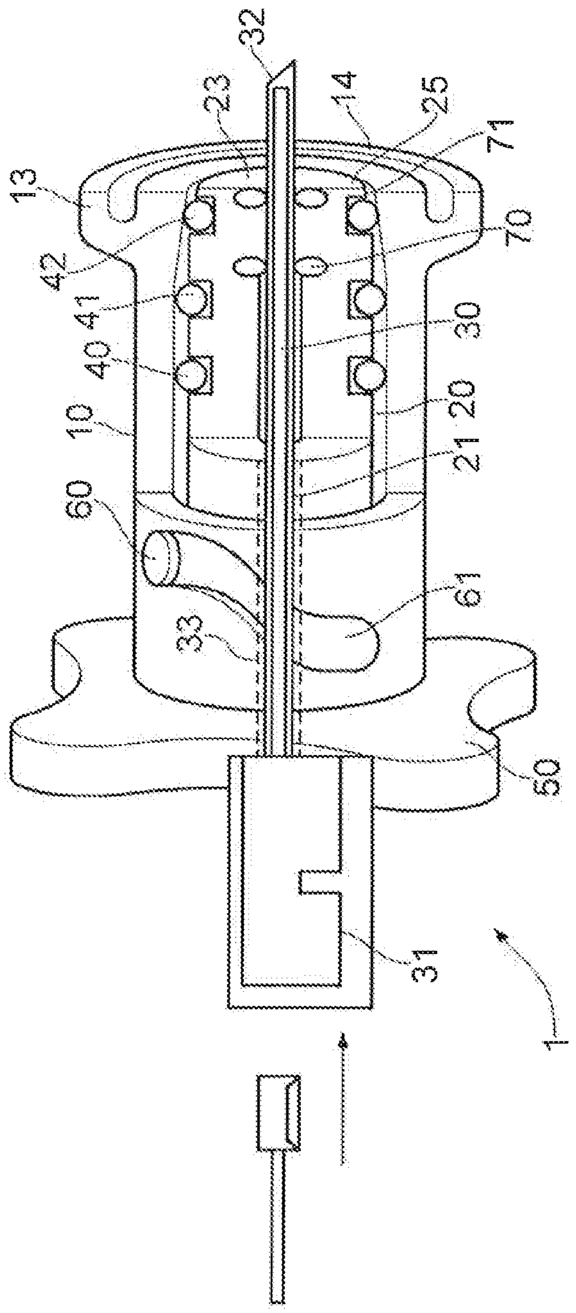
FIG. 8 shows an exemplary system of the invention with the probe secured within an insertion of the sensor probe and modified ReadyMate™ connection system.

In one embodiment and as illustrated in FIGS. 7 and 8, the system (1) of the present invention further comprises a cam (60) formed on an outer surface of the plunger (20) and contained within a cam slot (61) defined by the body (10), wherein said cam (60) is moveable between a first position within said cam slot (61) and a second position within said cam slot (61) and wherein said first position of said plunger (20) is concurrent with said first position of said cam (60) in said cam slot (61), and said second position of said plunger (20) is concurrent with said second position of said cam (60) in said cam slot (61).

In one embodiment of the system (1) of the present invention said plunger (20) is locked into said second position.

In one embodiment of the system (1) of the present invention the sensor end (32) of said sterile probe (30) comprises a sheath (32*a*, 32*b*).

In a second aspect, the present invention provides a sterile vessel (2) comprising one or more of the system (1) of the invention as defined hereinabove. FIGS. 2 and 4-7 illustrate examples of how a system (1) of the first aspect of the invention is connected to a sterile vessel (2).

Figure 2:
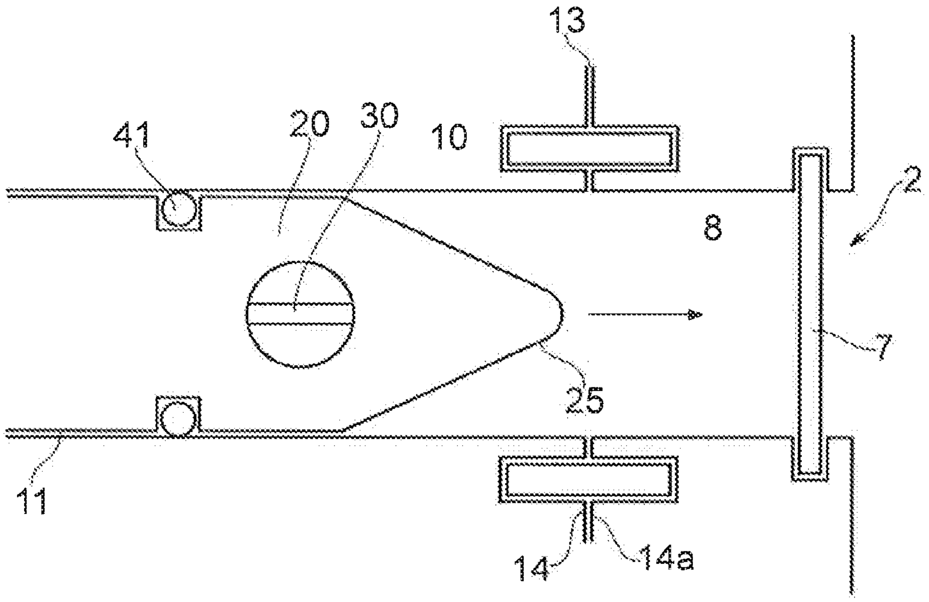
FIG. 2 is a cross-sectional view of an exemplary the second end of the plunger, which is in the form of a spike, advancing towards the sterile face connection and then the septum leading into the sterile vessel.

FIG. 2 shows an exemplary arrangement of the second end (13) of the body (10) and the corresponding second end (25) of the plunger (20) of the system (1) of the present invention. In FIG. 2 the body sterile face connection (14) and the vessel sterile face connection (14*a*) have been connected to create a sterile path (8) through which the plunger (20) can pass before piercing the septum (7) to enter the sterile vessel (2).

Figure 4:
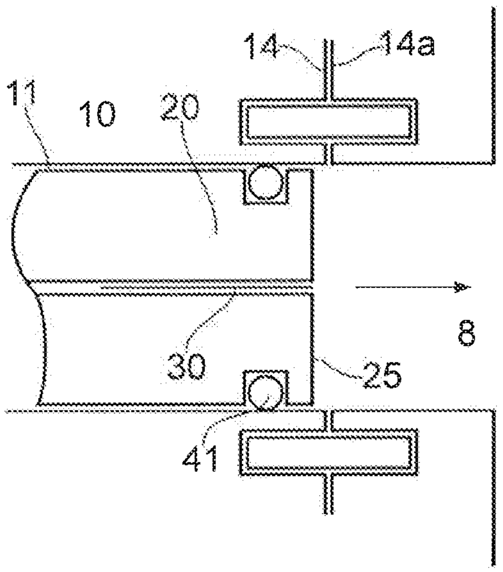
FIG. 4 is a cross-sectional view of an exemplary second end of the plunger having a flat configuration.

FIG. 4 also shows an example of how the second end (13) of the body (10) and the corresponding second end (25) of the plunger (20) may be positioned with respect to the sterile vessel (2) once the sterile face connectors (14, 14*a*) have been connected to create a sterile path (8) between the system (1) of the invention and the sterile vessel (2). The plunger (20) illustrated in FIG. 4 has a flat second end (25).

Figure 5:
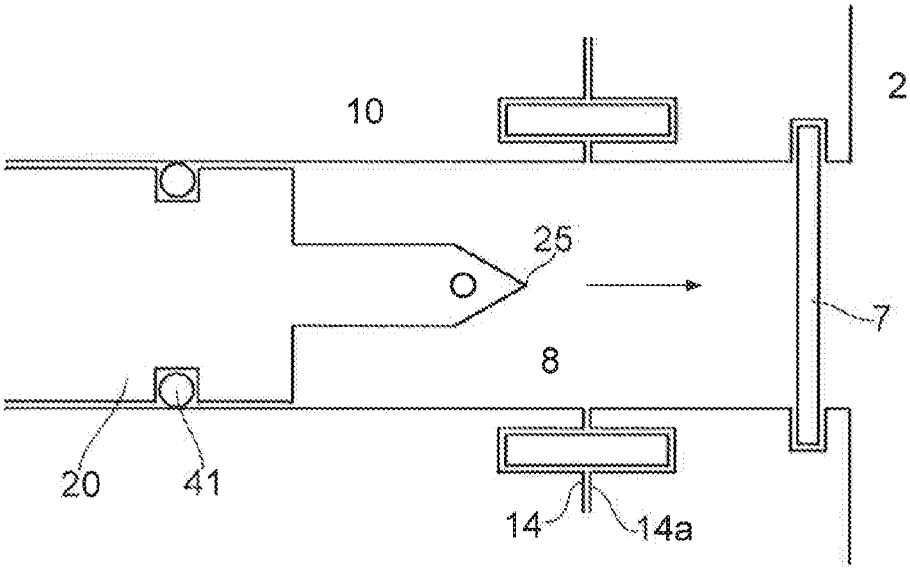
FIG. 5 shows a cross-sectional view of an exemplary second end of the plunger having a small septum spike as its second end.
Figure 6:
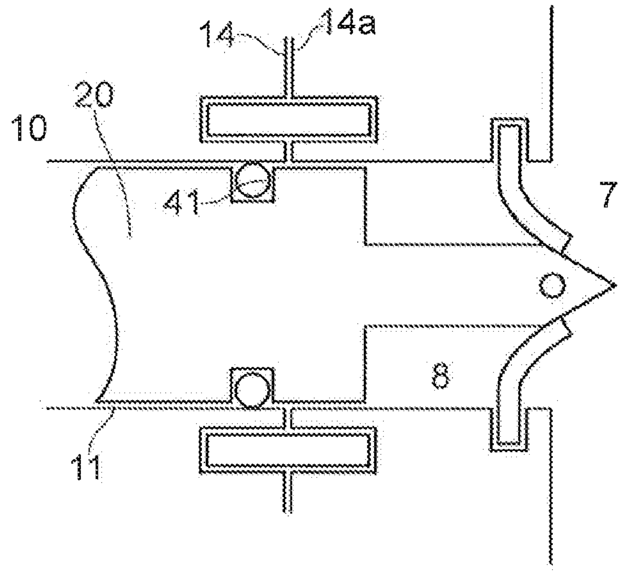
FIG. 6 is the plunger of FIG. 5 following insertion through the septum and into the sterile vessel.

Another exemplary plunger configuration is illustrated in FIG. 5 wherein the second end (25) of the plunger (20) is formed into a spike of narrower diameter to the main body of the plunger (20). A hole in the second end of the plunger allows the probe (30) contained therein (not visible in FIG. 5) to come into contact with liquid in the sterile vessel (2) once inserted through the septum (7). FIG. 6 shows the arrangement of FIG. 5 but where the plunger (20) has pierced the septum (7) and its second end (25) is within the sterile vessel (2).

Figure 3A:
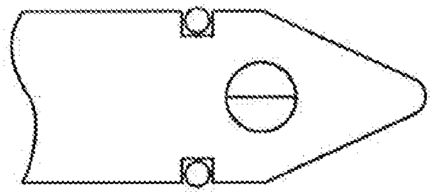
FIGS. 3A-3C illustrate exemplary configurations of the plunger having a spike configuration at its second end.
Figure 3B:
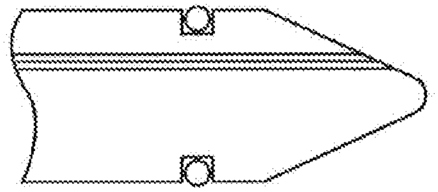
Figure 3C:
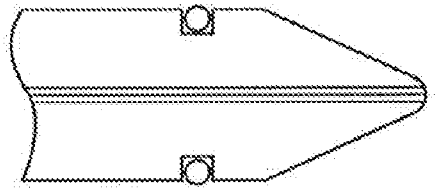
Figure 3D:
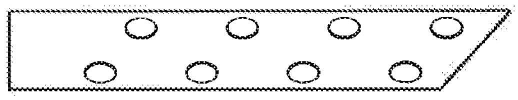
FIGS. 3D-3E illustrate exemplary configurations of probe sheaths suitable for use in the system of the invention.
Figure 3E:
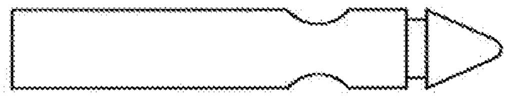

A selection of other spike arrangements is shown in FIGS. 3A-C. FIG. 3A shows a spike having an opening to the side to permit fluid flow into the sensor. FIG. 3B shows a spike at the second end of the plunger wherein the sensor lies nonaxially away from the spike in order to protect it as the plunger pierces the septum. Alternatively, where the sensor can withstand being pierced into the septum, an arrangement such as illustrated in FIG. 3C may be considered where the sensor is positioned axially in the plunger and protrudes from the second end of the plunger to act as a point.

FIGS. 3D and 3E show examples of probe sheaths that may be used to protect a delicate sensor while still permitting fluid to come into contact with the sensor. Such probe sheaths can also act as a point that protrudes from the second end of the plunger helping to pierce the septum.

The septum is a film or seal that can be punctured by the plunger and probe arrangement. In one embodiment, the septum creates a liquid-tight seal around the plunger after the plunger has pierced the septum so that no liquid from the sterile vessel enters the path between the system and the sterile vessel, i.e. no backward leaking. Suitable septa for use with the present invention will be well-known to those of skill in the art, e.g. made from an elastomeric material such as rubber or silicone.

In one embodiment the sterile vessel (2) of the invention is a biocontainer. In a more particular embodiment, the sterile vessel (2) is a bioreactor. In yet more particular embodiment the sterile vessel (2) is a flexible bag supported within a rigid holder. An example of this latter arrangement is illustrated in FIG. 1 where the inside of the flexible bag is shown by reference number (2), the wall of the bag by reference number (3), and the wall of the rigid holder by reference number (4). FIG. 1 also illustrates in cross-section an example of the system (1) where said sterile vessel comprises a wall (3) including a vessel sterile face connection (14*a*) and wherein said system (1) is connected to said sterile vessel (2) by mating said body sterile face connection (14) of said body (10) with said vessel sterile face connection (14*a*).

In one embodiment the sterile vessel (2) of the present invention comprises a wall (3) including a vessel sterile face connection (14*a*) and wherein the system (1) of the invention is connected to the sterile vessel (2) by mating said body sterile face connection (14) of the body (10) of said system (1) with said vessel sterile face connection (14*a*). In one embodiment, the body sterile face connection (14) and said vessel sterile face connection (14*a*) is each a single-use aseptic connection.

The system of the present invention allows for the placement of a sterile probe into a sterile vessel even when the sterile vessel is full. This is an advantage as it is preferred to insert expensive sensors after integrity testing of the sterile vessel. The presence of a septum on the side of the sterile vessel is helpful in this context as it acts to prevent the head pressure exerted by liquid in the vessel on the sterile face connection, which at least in the case of certain sterile face connectors may be relatively weak.

In one embodiment, the sterile vessel of the invention includes more than one of the system of the invention. This can be of particular use where the sterile vessel is relatively large. For example, when the sterile vessel is a 2000 L bioreactor bag, a problem can be very expensive to fix. Another scenario where this would be useful is where the sterile vessel is being used for a process that takes a relatively long time, i.e. beyond the life of just one probe. Having the facility to simply add a new probe at another site on the sterile vessel wall overcomes any issues encountered due to failures or life of the probe arrangement.

In a third aspect, the present invention provides a method for the insertion of a sterile probe (30) into a sterile vessel (2) wherein said sterile probe (30) is provided along with the system (1) of the invention as defined herein and wherein said sterile vessel (2) comprises a vessel sterile face connection (14*a*), wherein said method comprises:

(a) mating said body sterile face connection (14) of the body (10) of said system (1) with said vessel sterile face connection (14*a*);

(b) actuating the handle (50) of the plunger (20) of said system (1) so as to move said plunger (20) from said first to said second position.

In one embodiment, of the method of the present invention said actuating step comprises rotating said handle (50) around the longitudinal axis of said system (1).

All embodiments of the system (1) of the invention as described hereinabove are equally applicable to the sterile vessel (2) and the method of the invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A system for insertion of a sterile probe into a sterile biocontainer or a bioreactor, the system comprising:

a body comprising a sterile bore formed through at least a portion of an interior of the body, the body further comprising a first end and a second end, the second end comprising a body sterile face connection, wherein the body further comprises a sterilization port therethrough accessing the sterile bore;

a plunger contained within the sterile bore of the body, the plunger also having an inner channel opening onto a first aperture on a first end of the plunger and a second aperture on a second end of the plunger, wherein the first end and the second end of the plunger correspond respectively to the first end and the second end of the body, and wherein the plunger is moveable relative to the body between a first position and a second position;

a sterile probe positioned within the inner channel of the plunger, wherein the sterile probe comprises an electrical connection end, a sensor end, and a sensor body between the electrical connection end and the sensor end, and wherein the sterile probe is movable relative to the body between a retracted position within the body and an extended position with at least the sensor end outside the body by movement of the plunger between the first position and the second position; and one or more first seals positioned between the plunger and the sterile bore and configured to form a liquid-tight seal between respective portions of the plunger and the sterile bore.

2. The system of claim 1, wherein the sterile probe is selected from the group consisting of metabolic sensors, biologic sensors, and physical sensors.

3. The system of claim 2, wherein the sterile probe is a glucose sensor, a lactate sensor, a pH sensor, a temperature sensor, a conductivity sensor, or a cell mass and cell viability sensor.

4. The system of claim 1, wherein each of the body and the plunger is independently formed of a plastic selected from the group consisting of polyetherimides (PEI), polyetheretherketone (PEEK), polyetherketone (PEK), polysulphones, polyarylsulphones, polyalkoxysulphones, polyethersulphones, polyphenyleneoxide, polyphenylenesulphide, polycarbonate, and blends thereof.

5. The system of claim 1, further comprising a sterilization gas in the sterile bore and sterilization port.

6. The system of claim 1, further comprising one or more second seals positioned between the sterile probe and the inner channel of the plunger.

7. The system of claim 1, further comprising a handle coupled to the plunger and configured to rotate around a longitudinal axis of the system to direct movement of the plunger within the sterile bore between the first position and the second position.

8. The system of claim 7, wherein, between the first end of the plunger and the one or more first seals, the plunger comprises a plunger thread on an outer surface of the plunger, wherein the handle comprises a central opening configured to accommodate the plunger, and wherein the central opening comprises a handle thread that cooperates with the plunger thread such that rotational movement of the handle directs the movement of the plunger within the sterile bore between the first position and the second position.

9. The system of claim 8, wherein the central opening further comprises a recess, wherein the body further comprises a first notch protruding outwardly from a surface of the body and located substantially at first end of the body, and wherein the first notch is received in the recess.

10. The system of claim 9, wherein the body further comprises a second notch protruding outwardly from the surface of the body, and wherein the second notch provides mechanical support to the interaction of the first notch and the recess.

11. The system of claim 10, further comprising a cam formed on an outer surface of the plunger and contained within a cam slot defined by the body, wherein the cam is moveable between a first position within the cam slot and a second position within the cam slot, wherein the first position of the plunger is concurrent with the first position of the cam in the cam slot, and wherein the second position of the plunger is concurrent with the second position of the cam in the cam slot.

12. The system of claim 11, wherein the plunger is locked into the second position.

13. The system of claim 1, wherein the sensor end of the sterile probe comprises a sheath.

14. A sterile biocontainer comprising one or more of the system of claim 13.

15. A sterile bioreactor comprising one or more of the system of claim 13.

16. The sterile bioreactor of claim 15, wherein the sterile bioreactor comprises a flexible bag supported within a rigid holder.

17. The sterile bioreactor of claim 16, wherein the sterile bioreactor comprises a wall including a bioreactor sterile face connection, and wherein the body sterile face connection is mated with the bioreactor sterile face connection.

18. The sterile vessel of claim 17, wherein the body sterile face connection and the bioreactor sterile face connection are each a single-use aseptic connection.

19. A method for the insertion of a sterile probe into a sterile biocontainer or a bioreactor, wherein the sterile probe is provided as a part of the system as defined in claim 1, and wherein the sterile biocontainer or a bioreactor comprises a sterile face connection, the method comprising:

mating the body sterile face connection with the sterile face connection of the sterile biocontainer or a bioreactor; and moving the plunger from the first position to the second position.

* * * * *